United States Patent [19]

Marshall et al.

[11] 4,387,974

[45] Jun. 14, 1983

[54] CIRCUIT FOR CALCULATING THE POSITION OF THE EYE

[75] Inventors: Albert H. Marshall; Gary M. Bond, both of Orlando, Fla.

[73] Assignee: The United States of America as represented by the Secretary of the Navy, Washington, D.C.

[21] Appl. No.: 262,152

[22] Filed: May 11, 1981

[51] Int. Cl.³ .............................................. A61B 3/14
[52] U.S. Cl. .................................... 351/210; 351/209
[58] Field of Search ............................... 351/210, 209

[56] References Cited

U.S. PATENT DOCUMENTS 3,217,706 11/1965 Sullivan ............................... 128/734
3,473,868 10/1969 Young et al. ........................ 351/210
4,169,663 10/1979 Murr .................................... 351/210

Primary Examiner—John K. Corbin
Assistant Examiner—Paul M. Dzierzynski
Attorney, Agent, or Firm—Robert F. Beers; Robert W. Adams; Robert J. Veal

[57] ABSTRACT

An eye position measurement circuit is disclosed for calculating the position of the cornea of the human eye. The eye position measurement circuit includes a dual axis infrared light detector which will sense the position of the cornea of the eye upon receiving pulsed infrared light reflected from the cornea of the eye. The dual axis infrared light detector is, in turn, connected in unique combination with filters, absolute value circuits, analog-to-digital converters, latches, a digital computer, and other electronic components for calculating the position of the cornea of the human eye.

13 Claims, 6 Drawing Figures

A

B

C

A

B

C

D

E

F

G

CIRCUIT FOR CALCULATING THE POSITION OF THE EYE

BACKGROUND OF THE INVENTION

1. Field of the Invention

This invention relates generally to means for monitoring eye movement. In particular, this invention relates to an electronics circuit for calculating the position of a human eye at any given instant of time.

2. Description of the Prior Art

Heretofore numerous methods and apparatus have been employed for monitoring the position and movement of the human eye. Such apparatus are too numerous to discuss herewith. Besides, most thereof constitute prior art devices which are well known to the artisan, thereby obviating the need for further discussion thereof.

Of course, there are several prior art devices which are of some significance, inasmuch as they at least remotely or indirectly concern subject matter that is pertinent to the system constituting the instant circuit for calculating the position of the eye.

For example, U.S. Pat. No. 3,217,706 to G. H. Sullivan discloses an impedance oculograph which includes first and second pairs of electrodes adapted to be applied to the body surface near the eye, oscillator means for supplying a fixed amplitude carrier voltage to the first and second pairs of electrodes, first demodulator means connected to the first pair of electrodes for providing an electrical output signal corresponding to the vertical position of the eye with respect to a neutral position, and second demodulator means connected to the second pair of electrodes for providing an electrical output signal corresponding to the horizontal position of the eye with respect to the neutral position.

U.S. Pat. No. 3,473,868 to L. R. Young and J. S. Newman discloses a first pair of infrared light sensitive photo cells, which sense vertical eye movement, and a second pair of infrared light sensitive photocells, which sense horizontal eye movement. The output signals of the first pair of photocells are summed at a first transformer, amplified by a first operational amplifier, and fed to a first phase sensitive detector which produces an output signal only when an infrared light source is on. The output of the aforementioned detector is then directed through a filter which yields a DC signal proportional to vertical eye movement. In a like manner, the difference in the output signals of the second pair of photocells is determined by a second transformer, amplified by a second operational amplifier, and fed to a second phase sensitive detector which produces an output signal only when the above mentioned infrared light source is on. The output of the above mentioned detector is directed through a second filter so as to yield a DC signal which is a function of the horizontal eye position.

Unfortunately, the aforementioned devices of the prior art ordinarily leave something to be desired, especially from the standpoints of position measurement accuracy and response time, that is, the aforementioned devices of the prior art do not allow for position measurements at high rates. In addition, the aforementioned devices of the prior art do not operate in exactly the same manner as the subject invention and contain a combination of elements that is somewhat different from that of the present invention.

SUMMARY OF THE INVENTION

The subject invention overcomes some of the disadvantages of the prior art, including those mentioned above in that it comprises a relatively simple eye position measurement circuit which is responsive to pulsed infrared light rather than being responsive to ordinary light or other less coherent types of radiant energy. Consequently, it is far more sensitive which, in turn, makes it far more efficient and accurate in its response. Thus, vastly improved eye position measurement is the result of the use thereof.

Included in the subject invention is a dual axis infrared light detector adapted for sensing the position of the cornea of the human upon sensing the aforementioned pulsed infrared light reflected from the corneal area of the eye. The infrared light detector will provide a plurality of sinusoidal waveform signals indicative of the X and Y coordinate positions of the cornea of the eye within the field of view of the infrared light detector. The aforementioned signals are then processed by a unique combination of filters, absolute value circuits, analog-to-digital converters, latches, a microcomputer, and other logic components so as to determine the X coordinate position and the Y coordinate position of the cornea of the eye within the field of view of the aforesaid dual axis infrared light detector.

DESCRIPTION OF THE PREFERRED EMBODIMENT

Figure 1:
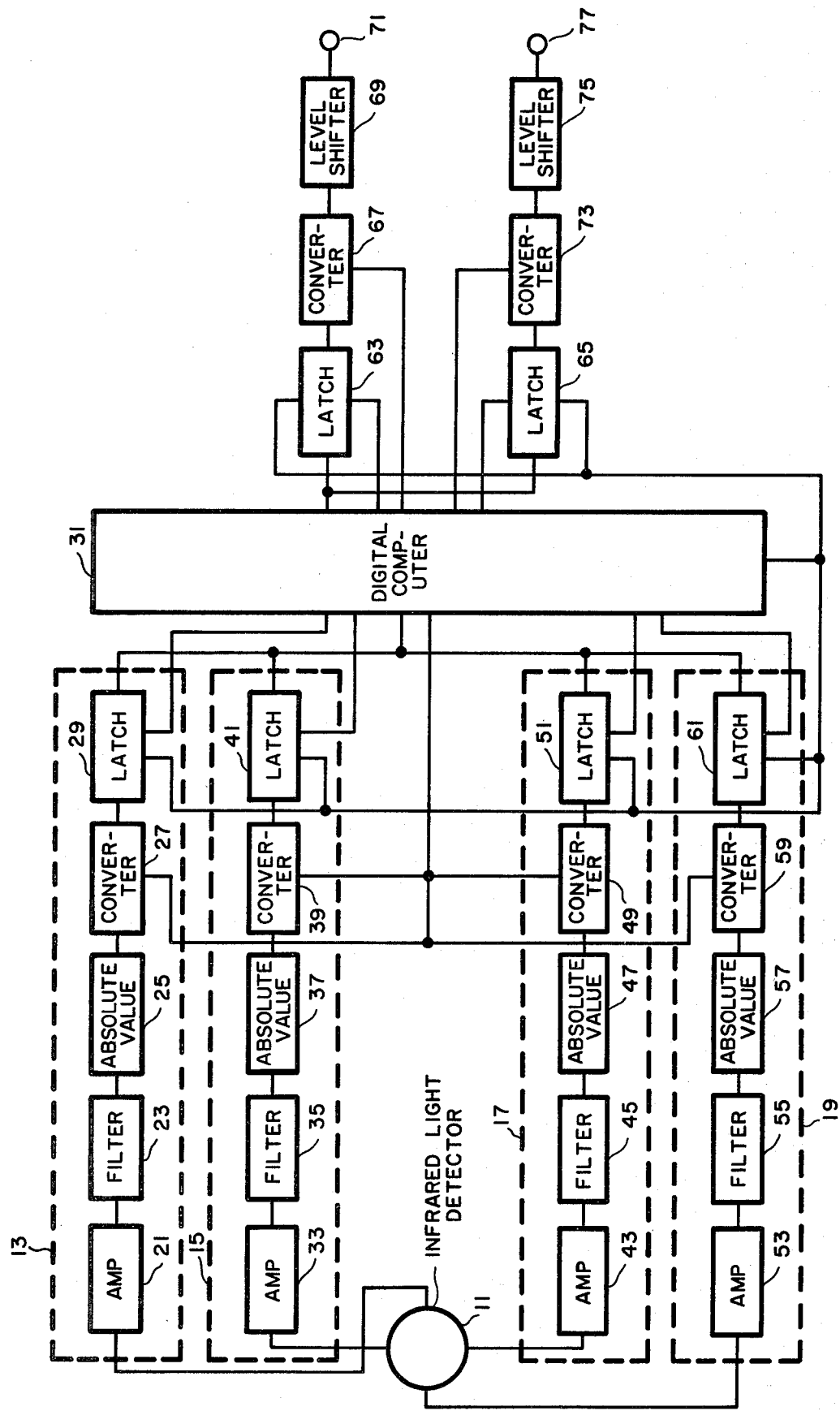
FIG. 1 illustrates in block diagram form the eye position calculating circuit constituting the subject invention.

The preferred embodiment of the subject invention will now be discussed in some detail in conjunction with all of the figures of the drawing wherein like parts are designated by like reference numerals, insofar as it is possible and practical to do so.

Referring now to FIG. 1, there is shown a dual axis infrared light detector 11 sensitive to infrared light, and, as will be discussed more fully below, measure movement of the cornea of a human eye. The aforementioned infrared light detector 11 may be utilized with a variety of eye trackers as the light sensing element therein such as the eye tracker disclosed in U.S. Patent Application entitled Helmet Mounted Eye Tracker Using Position Sensing Detector, Ser. No. 262,153, by Dennis Breglia, filed concurrently with this application.

The four outputs of infrared light detector 11 are, in turn, connected to the inputs of four data processing channels, herewith referenced by reference numerals 13, 15, 17, and 19, respectively.

The first output of infrared light detector, 11, for example, is connected to the input of an amplifier 21, the output of which is connected to the input of a bandpass filter 23, with the output thereof connected to the input of an absolute value circuit 25. The output of absolute value circuit 25 is connected to the data input of an analog-to-digital converter 27, the output of which is connected to the data input of a latch 29, with the output thereof connected to the data input of a microcomputer 31.

Similarly, the second output of infrared light detector 11 is connected to the input of an amplifier 33, the output of which is connected to the input of a bandpass filter 35, with the output thereof connected to the data input of an absolute value circuit 37. The output of absolute value circuit 37 is connected to the data input of an analog-to-digital converter 39, the output of which is connected to the data input of latch 41, with the output thereof connected to the data input of microcomputer 31.

Likewise, the third output of infrared light detector 11 is connected to the input of an amplifier 43, the output of which is connected to the input of a bandpass filter 45, with the output thereof connected to the input of an absolute value circuit 47. The output of absolute value circuit 47 is connected to the data input of an analog-to-digital converter 49, the output of which is connected to the data input of a latch 51, with the output thereof connected to the data input of microcomputer 31.

The fourth output of infrared light detector 11 is, in turn, connected to the input of an amplifier 53, the output of which is connected to the input of a bandpass filter 55, with the output thereof connected to the input of an absolute value circuit 57. The output of absolute value circuit 57 is connected to the data input of an analog-to-digital converter 59, the output of which is connected to the data input of a latch 61, with the output thereof connected to the data input of microcomputer 31.

The data output of microcomputer 31 is connected to the data input of a latch 63, and the data input of a latch 65. The output of latch 63 is connected to the data input of a digital-to-analog converter 67, the output of which is connected to the input of a voltage level shifter 69, with the output thereof connected to output terminal 71. Likewise, the output of latch 65 is connected to the data input of a digital-to-analog converter 73, the output of which is connected to the data input of a voltage level shifter 75, with the output thereof connected to output terminal 77.

The enable output of microcomputer 31 is connected to the enable input of latches 29, 41, 51, 61, 63, and 65. The first, second, third, fourth, fifth, and sixth select outputs of microcomputer 31 are respectively connected to the select inputs of latches 29, 41, 51, 61, 63, and 65. The seventh select output of microcomputer 31 is connected to the select input of analog-to-digital converters 27, 39, 49, and 59, while the eighth and ninth select outputs of microcomputer 31 are respectively connected to the select inputs of digital-to-analog converters 67 and 73.

In the exemplary circuit of FIG. 1 according to the invention components successfully utilized are as follows:

| Component | Reference Numeral | Model | Manufacturer |
|---|---|---|---|
| Amplifiers | 21,33,43,53 | TL082 | Texas Instruments |
| Analog-to-Digital Converters | 27,39,49, 59 | ADC0801 | National Semiconductor |
| Latches | 29,41,51,61, 63, and 65 | 8212 | Intel |
| Microcomputer | 31 | 8748 | Intel |
| Digital-to-Analog Converter | 67,73 | AD558 | Analog Devices |

Figure 2:
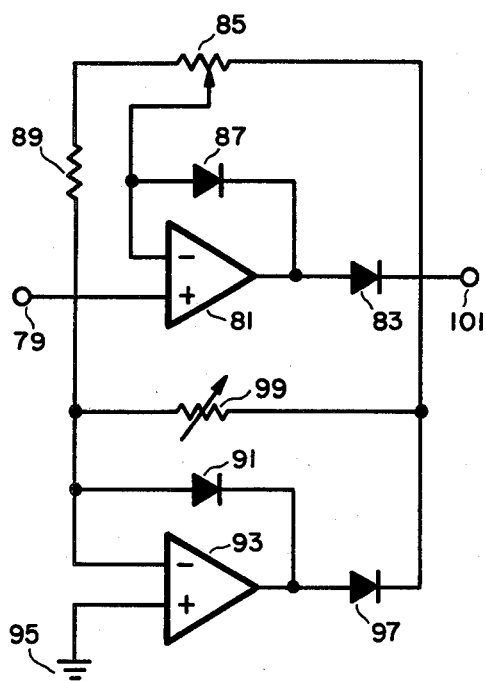
FIG. 2 shows a circuit diagram of one of the absolute value circuits of the invention of FIG. 1.

Referring now to FIG. 2, there is shown an absolute value circuit which may be any of the absolute value circuits 25, 37, 47, or 57 of the circuit of FIG. 1. The absolute value circuit of FIG. 2 includes therein an input terminal 79 connected to the positive input of an operational amplifier 81, the output of which is connected to the anode of a diode 83, with the cathode thereof connected to the first terminal of a variable resistor 85. The second terminal of variable resistor 85 is connected to the negative input of operational amplifier 81 and the anode of diode 87, the cathode of which is connected to the output of operational amplifier 81. The third terminal of variable resistor 85 is connected through a resistor 89 to the anode of a diode 91, and the negative input of an operational amplifier 93, the positive input of which is connected to a ground 95. The output of operational amplifier 93 is connected to the cathode of diode 91, and the anode of a diode 97, the cathode of which is connected to the cathode of diode 83. Connected between the negative input of operational amplifier 93 and the cathode of diode 97 is a variable resistor 99. In addition, the cathode of diode 97 is connected to an output terminal 101.

Figure 3:
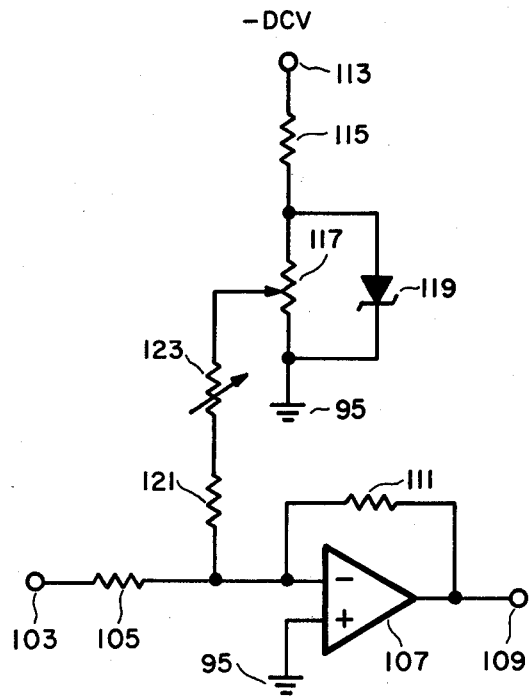
FIG. 3 shows a circuit diagram of one of the level shifting circuits of FIG. 1.

Referring now to FIG. 3, there is shown a voltage level shifter which may be either of the voltage level shifters 69 or 75 of the circuit of FIG. 1. The voltage level shifter of FIG. 3 includes therein an input terminal 103 connected through a resistor 105 to the negative input of an operational amplifier 107. The positive input of operational amplifier 107 is connected to ground 95, while the output of operational amplifier 107 is connected to an output terminal 109. Connected between the negative input and the output of operational amplifier 107 is a resistor 111. The output of a negative direct current voltage source 113 is connected through a resistor 115 to the first terminal of a variable resistor 117, the second terminal of which is connected to ground 95. Connected to the first terminal of variable resistor 117 is the anode of a Zener diode 119, while the cathode of the Zener diode 119 is connected to the second terminal of variable resistor 117. Connected between the negative terminal of operational amplifier 107 and the third terminal of variable resistor 117 is the series combination of a resistor 121 and a variable resistor 123.

Figure 4:
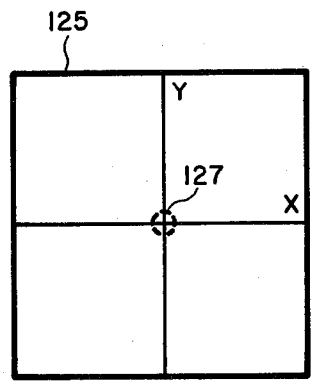
FIG. 4 depicts the field of view of the dual axis light detector of FIG. 1.

In addition, it should be noted at this time that FIG. 4 depicts the field of view or active area, generally designated by reference numeral 125, of dual axis infrared light detector 11. As will be discussed more fully below, dual axis infrared light detector 11 incorporates therein a dual axis or cartesian coordinate measuring system for monitoring the position of the cornea of the human eye.

The operation of the subject invention will now be discussed briefly in conjunction with all of the figures of the drawing.

Referring first to FIGS. 1 and 4, dual axis infrared light detector 11 monitors the movement of the cornea of the human eye by sensing pulsed infrared light reflected therefrom. The pulsed infrared light, the frequency of which is approximately ninety-six hertz may, of course, be provided by an infrared light source of the type utilized within the eye tracker described in the aformentioned U.S. patent application entitled Helmet Mounted Eye Tracker Using Position Sensing Detector, Ser. No. 262,153.

Upon receiving the pulsed infrared light reflected from the cornea of the human eye, infrared light detector 11 provides at each output thereof a square wave signal having a frequency of approximately ninety-six hertz.

As mentioned above, dual axis infrared light detector 11 incorporates therein a dual axis or cartesian coordinate measuring system for monitoring the position of the cornea of the human eye. The square wave signals provided at the first and second outputs of infrared light detector 11 are, in turn, indicative of the X position of the cornea of the human eye within field of view 125 of infrared light detector 11. Likewise, the square wave signals provided at the third and fourth outputs of infrared light detector 11 are indicative of the Y position of the cornea of the human eye within field of view 125 of infrared light detector 11. In addition, the sum of the amplitude of the square wave signals provided at the first and second outputs of infrared light detector 11 remains at a fixed or constant value, while the sum of the amplitudes of the square wave signals provided at the third and fourth outputs of infrared light detector 11 remains at a fixed or constant value.

As an example of the operation of dual axis infrared light detector 11, assume that infrared light detector 11 senses an infrared light spot 127 at the center of field of view 125, thereby indicating that the cornea of the human eye is positioned at the center of field of view 125 of infrared light detector 11. Infrared light detector 11 will then provide at the first and second outputs thereof, respectively, first and second square wave signals indicative of the X coordinate position of the cornea of the eye and having amplitudes of equal value. Likewise, infrared light detector 11 will provide at the third and fourth outputs thereof, respectively, third and fourth square wave signals indicative of the Y coordinate position of the cornea of the eye, and having amplitudes of equal value.

The first, second, third, and fourth square wave signals provided by infrared light detector 11 are respectively supplied to data processing channels 13, 15, 17, and 19 for processing thereby. Since all of the aforesaid four data processing channels 13, 15, 17, and 19 operate in exactly the same manner and for the sake of keeping this disclosure as simple as possible, only the operation of data processing channel 13 will be described.

Figure 5:
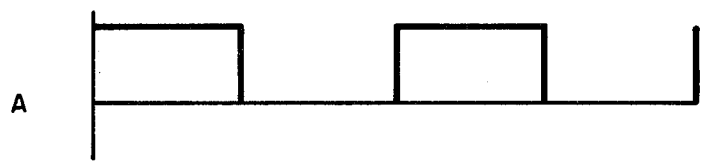
FIG. 5 is a graphical representation of various signal waveforms which occur at the outputs of some of the elements of FIG. 1.
Figure 5:
Figure 5:
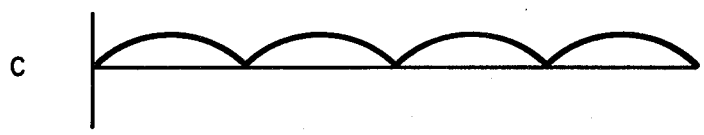

The square wave signal provided at the first output of infrared light detector 11, which is similar to that depicted in FIG. 5A, is supplied to the input of amplifier 21 for amplification thereby to a more useful voltage level, and then to the input of bandpass filter 23. Bandpass filter 23, in turn, filters from the signal of FIG. 5A any extraneous noise so as to provide at the output thereof a sine wave signal similar to that of FIG. 5B, and having a frequency of ninety-six hertz. The sine wave signal of FIG. 5B is then supplied to the input of absolute value circuit 25, which rectifies the aforementioned signal so as to provide at the output thereof a full wave rectified signal similar to that depicted in FIG. 5C.

With reference to FIG. 2, the operation of absolute value circuit 25 will now be discussed in detail. The signal of FIG. 5B is supplied through input terminal 79 to the positive input of operational amplifier 81. A positive input signal will cause the output of operational amplifier 81 to become positive thereby forward biasing diode 83, and reverse biasing diode 87. This, in turn, allows operation amplifier 81 to amplify the positive voltage portion of the sine wave signal of FIG. 5B, which then passes through diode 83 to output terminal 101.

At this time, it should be noted that the magnitude gain of operational amplifier 81 is controlled by variable resistor 85. In addition, it should be noted that a positive signal at the output of operational amplifier 81 will forward bias diode 91 such that diode 91 functions as a short circuit, thereby rendering operation amplifier 93 inactive.

A negative input signal applied to input terminal 79 will cause the output of operational amplifier 81 to become negative, thereby forward biasing diode 87 and reverse biasing diode 83. Since diode 87 now functions as a short circuit, operational amplifier 81 will perform as a voltage follower and supply the negative portion of the sine wave signal of FIG. 5B to operational amplifier 93.

A negative input signal applied to the negative input of operational amplifier 93 will cause the output of operational amplifier 93 to become positive, thereby reverse biasing diode 91 and forward biasing diode 97. Since diode 91 now functions as an open circuit, operational amplifier 93 will invert and amplify the negative portion of the sine wave signal of FIG. 5B which then passes through diode 97 to output termianl 101. This, in turn, results in the above mentioned full wave rectified signal of FIG. 5C appearing at output terminal 101. In addition, it should be noted that the magnitude gain of operational amplifier 93 is controlled by variable resistor 99.

Figure 6:
FIG. 6 is an expanded graphical illustration of one of the signals depicted in FIG. 5 and other internal component output signals of the system of FIG. 1 coordinated therewith.
Figure 6:
Figure 6:
Figure 6:
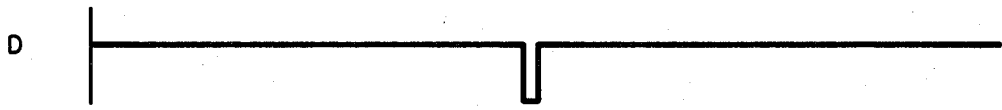
Figure 6:
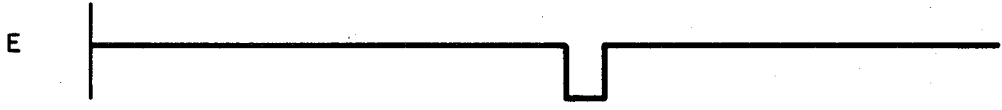
Figure 6:
Figure 6:

To facilitate the better understanding of that portion of the mode of operation of the invention to be discussed now, it would appear to be noteworthy to mention that the signal waveform of FIG. 6A is in fact identical to that of FIG. 5C; however, in the portrayal thereof in FIG. 6A, the time frame represented by the abscissa has been expanded so as to provide a frame that will permit the disclosure of the other signals shown in FIGS. 6B thru 6G.

The full wave rectified signal of FIG. 5C is supplied to the data input of analog-to-digital converter 27, which will then convert the aforementioned signal of FIG. 5C to a digital signal, or an eight bit digital word, upon receiving from microcomputer 31 a select pulse, similar to that depicted in FIG. 6B. Analog-to-digital converter 27 will then supply to the data input of latch 29 the aforementioned eight bit digital word. Latch 29 will, in turn, latch therein the digital word provided by analog-to-digital converter 27 upon receiving from microcomputer 31 an enable pulse similar to that of FIG. 6C. Upon receiving a select pulse similar to that of FIG. 6D from microcomputer 31, latch 29 will transfer to the data input of microcomputer 31 the digital word latched therein so as to allow for the processing of the aforementioned digital word in accordance with an eye position measurement program utilized by microcomputer 31. In a like manner the digital words stored within latched 41, 51, and 61 are transferred to microcomputer 31 for processing thereby.

Microcomputer 31 is programmed to calculate the position of the cornea of the eye by utilizing the aforementioned eye position measurement program. This, in turn, is accomplished by calculating the X coordinate position and the Y coordinate position of the cornea of the human eye within field of view 125 of infrared light detector 11 in accordance with the following relationships.

$$X = (|X_1 - X_2|)/(X_1 + X_2) \quad (1)$$

$$Y = (|Y_1 - Y_2|)/(Y_1 + Y_2) \quad (2)$$

where X and Y are respectively the X and Y coordinate positions of the cornea of the human eye within field of view 125 of infrared light detector 11 and $X_1$, $X_2$, $Y_1$ and $Y_2$ are the numerical equivalent of the digital words provided by, respectively, data processing channels 13, 15, 17, and 19.

For the example discussed previously, in which infrared light spot 127 is positioned at the center of field of view 125 of light detector 11, $X_1$ and $X_2$ are equivalent such that the value of X calculated in accordance with relationship one above will be zero. Likewise, for the above identified example, $Y_1$ and $Y_2$ are equivalent such that the value of Y calculated in accordance with relationship two above will be zero.

Microcomputer 31 will then provide at the data output thereof digital signals or eight bit digital words indicative respectively of the X and Y coordinate positions of the cornea of the human eye within field of view 125 of infrared light detector 11. For the example described above, the digital words provided at the data output of microcomputer 31 will each have a decimal value of 128, thereby indicating that the cornea of the human eye is positioned at the center of field of view 125 of infrared light detector 11.

In addition, it should be noted, for example, that a digital word appearing at the data output of microcomputer 31 having a decimal equivalent of zero may indicate that infrared light spot 127 is positioned at the extreme right of the X coordinate axis of field of view 125, while a digital word appearing at the data output of microcomputer 31 having a decimal equivalent of 255 may indicate that the infrared light spot 127 is positioned at the extreme left of the X coordinate axis of field of view 125. Likewise, a digital word appearing at the data output of microcomputer 31 having a decimal equivalent of zero may indicate that infrared light spot 127 is positioned at the uppermost part of the Y coordinate axis of field of view 125, while a digital word appearing at the data output of microcomputer 31 having a decimal equivalent of 255 may indicate that infrared light spot 127 is positioned at the lowermost part of the Y coordinate axis of field of view 125. Because the operation of components 63, 67, and 69 upon the digital words provided at the data output of microcomputer 31 is identical to the operation of components 65, 73, and 75 upon the digital words provided at the data output of computer 31, and for the sake of keeping this disclosure as simple as possible only the operation of components 63, 67, and 69 will be described.

Upon receiving from microcomputer 31 an enable pulse similar to that depicted in FIG. 6E, latch 63 will latch therein the digital word, indicative of the X coordinate position of the eye within field of view 125, provided at the data output thereof. Latch 31 will then transfer the aforementioned digital word to the data input of digital-to-analog converter 67 upon receiving from microcomputer 31 a select pulse similar to that depicted in FIG. 6F.

Upon receiving from microcomputer 31 a select pulse similar to that of FIG. 6G, digital-to-analog converter 73 will convert the digital word supplied to the data input thereof to a direct current voltage signal having a voltage range from zero volts to 2.55 volts. The aforementioned direct current voltage signal, in turn, is indicative of the X coordinate position of the cornea of the eye within field of view 125 to infrared light detector 11.

The direct current voltage signal provided by digital-to-analog converter 67 is supplied to the data input of level shifter 69 which will shift the voltage level thereof such that the voltage range of the aforesaid direct current voltage signal at the output of level shifter 69 will be from approximately $-1.27$ volts to $+1.28$ V. For the example discussed previously, the signals appearing at output terminals 71 and 77 will have voltage levels of zero volts, thereby indicating that infrared light spot 127 is positioned at the center of field of view 125 of infrared light detector 11.

With reference to FIG. 3, the operation of voltage level shifter 69 will now be discussed. The direct current provided negative direct current voltage source 113 when passed through resistor 115 will cause Zener diode 119 to break down such that there is a voltage drop of approximately two volts across Zener diode 119. This, in turn, allows for the adjustment of variable resistors 117 and 123 so as to level shift the direct current voltage signal provided by digital-to-analog converter 67 from a voltage level of 0 to 2.55 volts to a voltage level of $-1.27$ to 1.28 volts when the aforesaid direct current voltage signal is passed through operational amplifier 107.

From the foregoing, it may readily be seen that the subject invention comprises a new, unique, and exceedingly useful circuit for calculating the position of the eye which constitutes a considerable improvement over the known prior art. Obviously, many modifications and variations of the present invention are possible in light of the above teachings. It is, therefore, to be understood that within the scope of the appended claims the invention may be practiced otherwise than as specifically described.

What is claimed is:

1. A circuit for calculating the position of the cornea of a human eye comprising in combination:

detecting means having a field of view and a quartet of outputs for sensing a pulsed infrared light reflected from the cornea of said human eye and for providing a quartet of square wave signals indicative of the X coordinate position and the Y coordinate position of the cornea of said human eye within the field of view of said detecting means;

a quartet of filtering means, each of which has an input connected to one of the outputs of said detecting means and an output, and each of which is adapted for removing from one of said quartet of square wave signals any extraneous noise so as to provide at the output thereof a sinusoidal waveform signal;

a quartet of absolute value circuit means, each of which has an input connected to the output of one of said quartet of filtering means and an output, and each of which is adapted for rectifying one of said sinusoidal waveform signals so as to provide at the output thereof a full wave rectified signal;

a quartet of analog-to-digital converting means, each of which has a data input connected to the output of one of said quartet of absolute value circuit means, and an output, and each of which is adapted for producing digital signals in response to one of said full wave rectified signals;

a quartet of latching means, each of which has a data input connected to the output of one of said analog-to-digital converting means, a select input, and an output, and each of which is adapted for storing therein the digital signals produced by one of said analog-to-digital converting means;

computing means having a data input effectively connected to the outputs of said quartet of latching means, first, second, third and fourth select outputs respectively connected to the select inputs of said quartet of latching means, a fifth select output, a sixth select output, and a data output for providing first, second, third and fourth select signals for effecting the transfer of the digital signals stored within said latching means from said latching means to the data input of said computing means, for calculating, in accordance with an eye position measurement program, the X and Y coordinate positions of the cornea of said human eye within the field of view of said detecting means, for providing at the data output thereof digital signals indicative of the X coordinate position of the cornea of said human eye within the field of view of said detecting means and for providing at the data output thereof digital signals indicative of the Y coordinate position of the cornea of said human eye within the field of view of said detecting means; and a pair of digital-to-analog converting means, each digital-to-analog converting means of which has an input connected to the data output of said computing means and an output, the first digital-to-analog converting means of which is adapted for producing analog signals in response to said digital signals indicative of the X coordinate positions of the cornea of said human eye within the field of view of said detecting means, and the second digital-to-analog converting means of which is adapted for producing analog signals in response to said digital signals indicative of the Y coordinate positions of the cornea of said human eye within the field of view of said detecting means.

2. The circuit of claim 1 wherein said detecting means comprises a dual axis infrared light detector.

3. The circuit of claim 1 wherein each of said quartet of filtering means comprises a bandpass filter.

4. The circuit of claim 1 wherein each of said quartet of absolute value circuit means comprises:

an input terminal connected to the output terminal of one of said quartet of filtering means;

a first operational amplifier having a positive input connected to said input terminal, a negative input, and an output;

a first diode having an anode connected to the output of said first operational amplifier and a cathode;

a second diode having an anode connected to the negative input of said first operational amplifier and a cathode connected to the output of said first operational amplifier;

a first variable resistor having first, second, and third terminals with the first terminal thereof connected to the negative input of said first operational amplifier, and with the second terminal thereof connected to the cathode of said first diode;

a ground;

a second operational amplifier having a negative input connected to the third terminal of said first variable resistor, a positive terminal connected to said ground, and an output;

a third diode having an anode connected to the negative input of said second operational amplifier, and a cathode connected to the output of said second operational amplifier;

a fourth diode having an anode connected to the output of said second operational amplifier, and a cathode connected to the cathode of said first diode;

a second variable resistor connected between the negative input of said second operational amplifier and the anode of said fourth diode; and an output terminal connected to the cathode of said first diode.

5. The circuit of claim 1 further characterized by a quartet of amplifiers, the first amplifier of which is connected between the first output of said detecting means and the input of said first filtering means, the second amplifier of which is connected between the second output of said detecting means and the input of said second filtering means, the third amplifier of which is connected between the third output of said detecting means and the input of said third filtering means, and the fourth amplifier of which is connected between the fourth output of said detecting means and the input of said fourth filtering means.

6. The circuit of claim 1 further characterized by a pair of latches, the first latch of which has a data input connected to the data output of said computing means, a select input connected to the fifth select output of said computing means, and an output connected to the input of said first digital-to-analog converting means, and the second latch of which has a data input connected to the data output of said computing means, a select input connected to the sixth select output of said computing means, and an output connected to the input of said second digital-to-analog converting means.

7. The circuit of claim 1 further characterized by first and second voltage level shifters, the first voltage level shifter of which has an input connected to the output of the first of said pair of digital-to-analog converting means, and the second voltage level shifter of which has an input connected to the output of the second of said pair of digital-to-analog converting means.

8. The circuit of claim 7 wherein each of said pair of voltage level shifters comprises:

an input terminal effectively connected to the output of one of said pair of digital-to-analog converting means;

a ground;

an operational amplifier having a negative input connected to said input terminal, a positive input connected to said ground, and an output;

a first resistor connected between said input terminal, and the negative input of said operational amplifier;

a second resistor connected between the negative input of said operational amplifier and the output of said operational amplifier;

a direct current voltage source having an output;

a first variable resistor having first, second, and third terminals, the first terminal of which is connected to the output of said direct current voltage source, and the second terminal of which is connected to said ground;

a Zener diode having an anode connected to the first terminal of said first variable resistor, and a cathode connected to the second terminal of said first variable resistor;

a third resistor connected between the output of said direct current voltage source and the first terminal of said first variable resistor; and the series combination of a fourth resistor and a second variable resistor connected between the negative input of said operational amplifier and the third terminal of said first variable resistor.

9. A position monitoring circuit comprising in combination:

a dual axis light detector having first, second, third and fourth outputs;

a first bandpass filter having an input connected to the first output of said dual axis light detector and an output;

a second bandpass filter having an input connected to the second output of said dual axis light detector and an output;

a third bandpass filter having an input connected to the third output of said dual axis light detector and an output;

a fourth bandpass filter having an input connected to the fourth output of said dual axis detector and an output;

a first absolute value circuit having an input connected to the output of said first bandpass filter and an output;

a second absolute value circuit having an input connected to the output of said second bandpass filter and an output;

a third absolute value circuit having an input connected to the output of said third bandpass filter and an output;

a fourth absolute value circuit having an input connected to the output of said fourth bandpass filter and an output;

a first analog-to-digital converter having a data input connected to the output of said first absolute value circuit, a select input, and an output, a second analog-to-digital converter having a data input connected to the output of said second absolute value circuit, a select input and an output;

a third analog-to-digital converter having a data input connected to the output of said third absolute value circuit, a select input, and an output;

a fourth analog-to-digital converter having a data input connected to the output of said fourth absolute value circuit, a select input, and an output;

a first latch having a data input connected to the output of said first analog-to-digital converter, an enable input, a select input, and an output;

a second latch having a data input connected to the output of said second analog-to-digital converter, an enable input, a select input, and an output;

a third latch having a data input connected to the output of said third analog-to-digital converter, an enable input, a select input, and an output;

a fourth latch having a data input connected to the output of said fourth analog-to-digital converter, an enable input, a select input, and an output;

a microcomputer having a data input respectively connected to the data outputs of said first, second, third and fourth latches, an enable output connected to the enable inputs of said first, second, third, and fourth latches, a data output, and nine select outputs, the first, second, third, and fourth select outputs of which are respectively connected to the select inputs of first, second, third, and fourth latches, and the fifth select output of which is connected to the select inputs of said first, second, third and fourth analog-to-digital converters;

a fifth latch having a data input connected to the data output of said microcomputer, an enable input connected to the enable output of said microcomputer, a select input connected to the sixth select output of said microcomputer, and an output;

a sixth latch having a data input connected to the data output of said microcomputer, an enable input connected to the enable output of said microcomputer, a select input connected to the seventh select output of said microcomputer, and an output;

a first digital-to-analog converter having a data input connected to the output of said fifth latch, a select input connected to the eighth select output of said microcomputer, and an output; and a second digital-to-analog converter having a data input connected to the output of said sixth latch, a select input connected to the ninth select output of said microcomputer, and an output.

10. The position monitoring circuit of claim 9 wherein said first, second, third, and fourth absolute value circuits each comprise:

an input terminal;

a first operational amplifier having a positive input connected to said input terminal, a negative input, and an output;

a first diode having an anode connected to the output of said first operational amplifier and a cathode;

A second diode having an anode connected to the negative input of said first operational amplifier and a cathode connected to the output of said first operational amplifier;

a first variable resistor having first, second and third terminals, with the first terminal thereof connected to the negative input of said first operational amplifier, and with the second terminal thereof connected to the cathode of said first diode;

a ground;

a second operational amplifier having a negative input connected to the third terminal of said first variable resistor, a positive terminal connected to said ground, and an output;

a third diode having an anode connected to the negative input of said second operational amplifier, and a cathod connected to the output of said second operational amplifier;

a fourth diode having an anode connected to the output of said second operational amplifier, and a cathode connected to the cathode of said first diode;

a second variable resistor connected between the negative input of said second operational amplifier and the anode of said fourth diode; and an output terminal connected to the cathode of said first diode.

11. The position monitoring circuit of claim 9 further characterized by a quartet of amplifiers, the first amplifier of which is connected between the first output of said dual axis light detector and the input of said first bandpass filter, the second amplifier of which is connected between the second output of said dual axis light detector and the input of said second bandpass filter, the third amplifier of which is connected between the third output of said dual axis light detector and the input of said third bandpass filter, and the fourth amplifier of which is connected between the fourth output of said dual axis light detector and the input of said fourth bandpass filter.

12. The position monitoring circuit of claim 9 further characterized by first and second voltage level shifters, the first voltage level shifter of which has an input connected to the output of said first digital-to-analog converter, and the second voltage level shifter of which has an input connected to the output of second digital-to-analog converter.

13. The position monitoring circuit of claim 12 wherein said first and second voltage level shifters each comprise:

an input terminal;
a ground;
an operational amplifier having a negative input connected to said input terminal, a positive input connected to said ground, and an output;
a first resistor connected between said input terminal, and the negative input of said operational amplifier;
a second resistor connected between the negative input of said operational amplifier and the output of said operational amplifier;
a direct current voltage source having an output;
a first variable resistor having first, second, and third terminals, the first terminal of which is connected to the output of said direct current voltage source, and the second terminal of which is connected to said ground;
a Zener diode having an anode connected to the first terminal of said first variable resistor, and a cathode connected to the second terminal of said first variable resistor;
a third resistor connected between the output of said direct current voltage source and the first terminal of said first variable resistor; and
the series combination of a fourth resistor and a second variable resistor connected between the negative input of said operational amplifier and the third terminal of said first variable resistor.

* * * * *